United States Patent
Malhotra et al.

(10) Patent No.: US 11,207,319 B2
(45) Date of Patent: *Dec. 28, 2021

(54) METHOD FOR THE TREATMENT OF BLADDER CANCER

(71) Applicant: Cipla Limited, Mumbai (IN)

(72) Inventors: Geena Malhotra, Mumbai (IN); Kalpana Joshi, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/181,651

(22) Filed: Nov. 6, 2018

(65) Prior Publication Data

US 2019/0247389 A1    Aug. 15, 2019

Related U.S. Application Data

(63) Continuation of application No. 15/370,393, filed on Dec. 6, 2016, now Pat. No. 10,149,848.

(30) Foreign Application Priority Data

Dec. 9, 2015    (IN) .................. 4641/MUM/2015

(51) Int. Cl.
  *A61K 31/496*    (2006.01)
  *A61K 33/24*    (2019.01)
  *A61K 31/4196*    (2006.01)
  *A61K 33/243*    (2019.01)
  *A61K 45/06*    (2006.01)

(52) U.S. Cl.
  CPC ........ *A61K 31/496* (2013.01); *A61K 31/4196* (2013.01); *A61K 33/24* (2013.01); *A61K 33/243* (2019.01); *A61K 45/06* (2013.01)

(58) Field of Classification Search
  CPC .. A61K 31/496; A61K 31/4196; A61K 33/24; A61K 33/243
  See application file for complete search history.

(56) References Cited

U.S. PATENT DOCUMENTS

| | | | |
|---|---|---|---|
| 4,358,449 A | 11/1982 | Heeres et al. | |
| 10,149,848 B2 * | 12/2018 | Malhotra | A61K 31/496 |
| 2006/0241122 A1 | 10/2006 | Lee et al. | |
| 2008/0193499 A1 | 8/2008 | Liu et al. | |

FOREIGN PATENT DOCUMENTS

WO    2006004795 A2    1/2006

OTHER PUBLICATIONS

Tournigand et al. Journal of Clinical Oncology, 2004, vol. 22, No. 2, pp. 229-237 (Year: 2004).*
Chong, et al., "Inhibition of Angiogenesis by the Antifungal Drug Itraconazole", ACS Chem. Biol. vol. 2 No. 4, 2007, 263-270.
Kinobe, et al., "Inhibition of the Enzymatic Activity of Heme Oxygenases by Azole-Based Antifungal Drugs", The Journal of Pharmacology and Experimental Therapeutics vol. 319 No. 1, 2006, 277-284.
Miyata, et al., "Heme oxygenase-1 expression is associated with tumor aggressiveness and outcomes in patients with bladder cancer: a correlation with smoking intensity", Translational Research vol. 164, No. 6, 2014, 468-476.
Shim, et al., "Recent Advances in Drug Repositioning for the Discovery of New Anticancer Drugs", Int. J. Biol. Sci. vol. 10, 2014, 654-663.
Babjuk et al., "EAU Guidelines on Non-Muscle-invasive Urothelial Carcinoma of the Bladder: Update 2013" European Urology, 2013, vol. 64, pp. 639-653.

* cited by examiner

*Primary Examiner* — James D. Anderson
(74) *Attorney, Agent, or Firm* — Meunier Carlin & Curfman LLC

(57) ABSTRACT

Methods of treating bladder cancer using terconazole are disclosed herein. Terconazole can be administered as part of a comprehensive treatment program, which can also include chemotherapy, immunotherapy, radiation therapy and/or surgical treatment.

4 Claims, 4 Drawing Sheets

METHOD FOR THE TREATMENT OF BLADDER CANCER

CROSS REFERENCE TO RELATED APPLICATION

This application is a continuation of U.S. application Ser. No. 15/370,393, filed Dec. 6, 2016, and issued as U.S. Pat. No. 10,149,848, which claims the benefit of Indian Application 4641/MUM/2015, filed Dec. 9, 2015, the contents of which are incorporated by reference.

FIELD OF THE INVENTION

The present invention is directed to a method of treating bladder cancer using terconazole or a pharmaceutically acceptable salt thereof.

BACKGROUND

Bladder cancer is a life-threatening and progressive disease, which usually begins in the lining of the epithelial lining (i.e., the urothelium) of the urinary bladder. Invasive bladder cancer may spread to lymph nodes, other organs in the pelvis (causing problems with kidney and bowel function), or other organs in the body, such as the liver and lungs. Standard treatments for bladder cancer are surgery, radiation therapy, chemotherapy, and biological therapy Bladder cancer is diagnosed using cystoscopy and/or cytology, however, the latter is not very sensitive—a negative result cannot reliably exclude bladder cancer.

There are newer non-invasive urine bound markers available as aids in the diagnosis of bladder cancer, including human complement factor H-related protein, high-molecular-weight carcinoembryonic antigen, and nuclear matrix protein 22 (NMP22). NMP22 is also available as a prescription home test. Other non-invasive urine based tests include the CertNDx Bladder Cancer Assay, which combines FGFR3 mutation detection with protein and DNA methylation markers to detect cancers across stage and grade, UroVysion, and Cxbladder. The diagnosis of bladder cancer can also be done with a Hexvix/Cysview guided fluorescence cystoscopy (blue light cystoscopy, Photodynamic diagnosis), as an adjunct to conventional white-light cystoscopy. This procedure improves the detection of bladder cancer and reduces the rate of early tumor recurrence, compared with white light cystoscopy alone. Cysview cystoscopy detects more cancer and reduces recurrence. Cysview is marketed in Europe under the brand name Hexvix.

The treatment of bladder cancer depends on how far cancer has spread. Most bladder cancer is found early, before it has spread into the bladder wall. Surgically, bladder cancer can be treated using transurethral resection of bladder tumor (TURBT), wherein the bladder is accessed using a cystoscope passed through the urethra to remove cancerous cells. In more severe cases, a partial or radical cystectomy may be performed. However, because of concerns regarding recurrence, patients often receive chemotherapy or immunotherapy in addition to surgery. Chemotherapies which have been employed include methotrexate, vinblastine, doxorubicin, and cisplatin (MVAC), gemcitabine and cisplatin (GC). Administration of these drugs is often accompanied by severe negative side effects.

Immunotherapies include intravesicular delivery of Bacillus Calmette-Guérin (BCG). BCG is a vaccine against tuberculosis that is prepared from attenuated (weakened) live bovine *tuberculosis bacillus, Mycobacterium bovis* that has lost its virulence in humans. BCG immunotherapy is effective in up to 66% of the cases at this stage, and in randomized trials has been shown to be superior to standard chemotherapy. The mechanism by which BCG prevents recurrence is unknown, but the presence of bacteria in the bladder may trigger a localized immune reaction which clears residual cancer cells. However, bladder cancer recurring in patients subsequent to BCG treatment is more difficult to treat.

There remains a need for effective, non-surgical treatments of bladder cancer, including bladder cancer recurring post-BCG treatment. There remains a need for agents effective to treat bladder cancer with reduced side effect profiles relative to currently used medications.

SUMMARY

Disclosed herein are methods of treating bladder cancer, including bladder cancer recurring post-BCG treatment. The methods include administering to a patient in need thereof terconazole in an amount effective to treat the bladder cancer. In some instances, terconazole can be administered as part of a combination therapy. Also disclosed herein are pharmaceutical compositions containing terconazole suitable for the treatment of bladder cancer. In some instances, the compositions include an additional anti-cancer agent.

The details of one or more embodiments are set forth in the descriptions below. Other features, objects, and advantages will be apparent from the description and from the claims.

DETAILED DESCRIPTION

Figure 1:
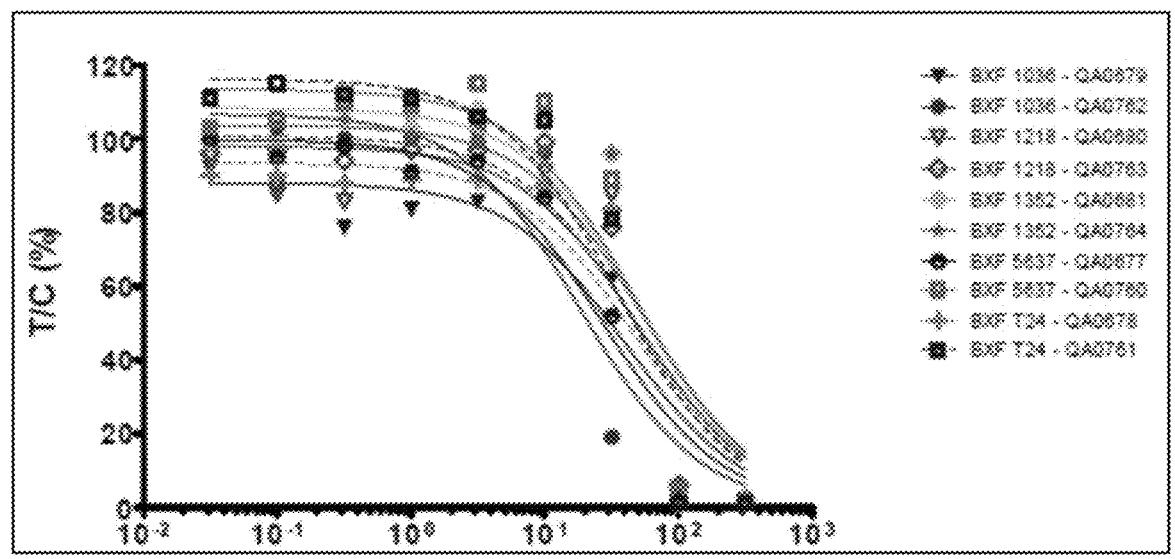
FIG. 1 includes a depiction of a 2D assay of terconazole against human bladder cancer cells.
Figure 2:
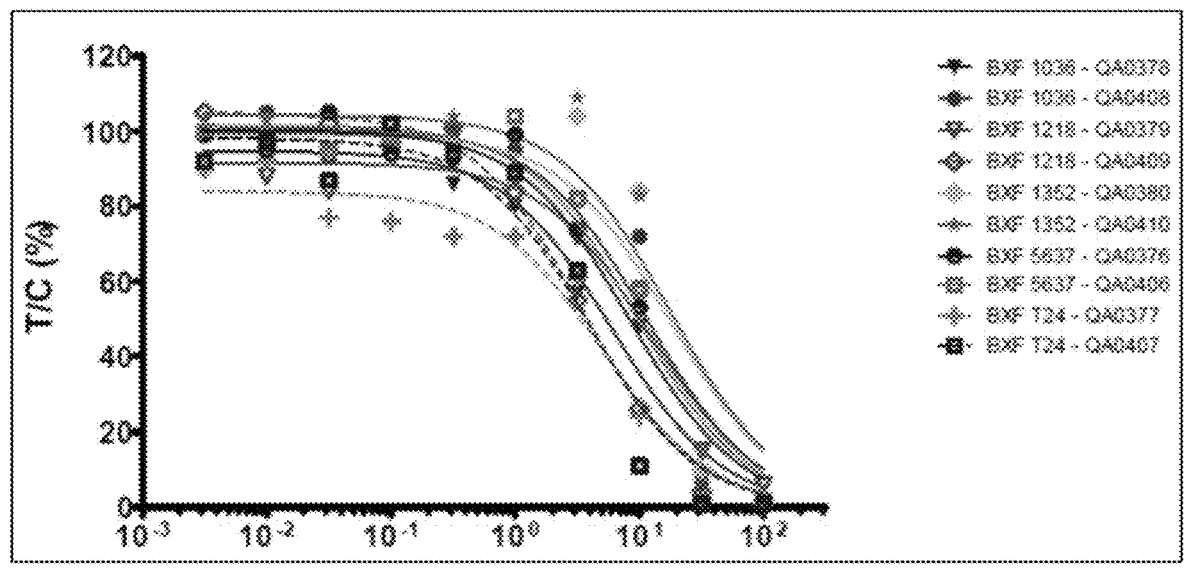
FIG. 2 includes a depiction of a 2D assay of cisplatin against human bladder cancer cells.
Figure 3:
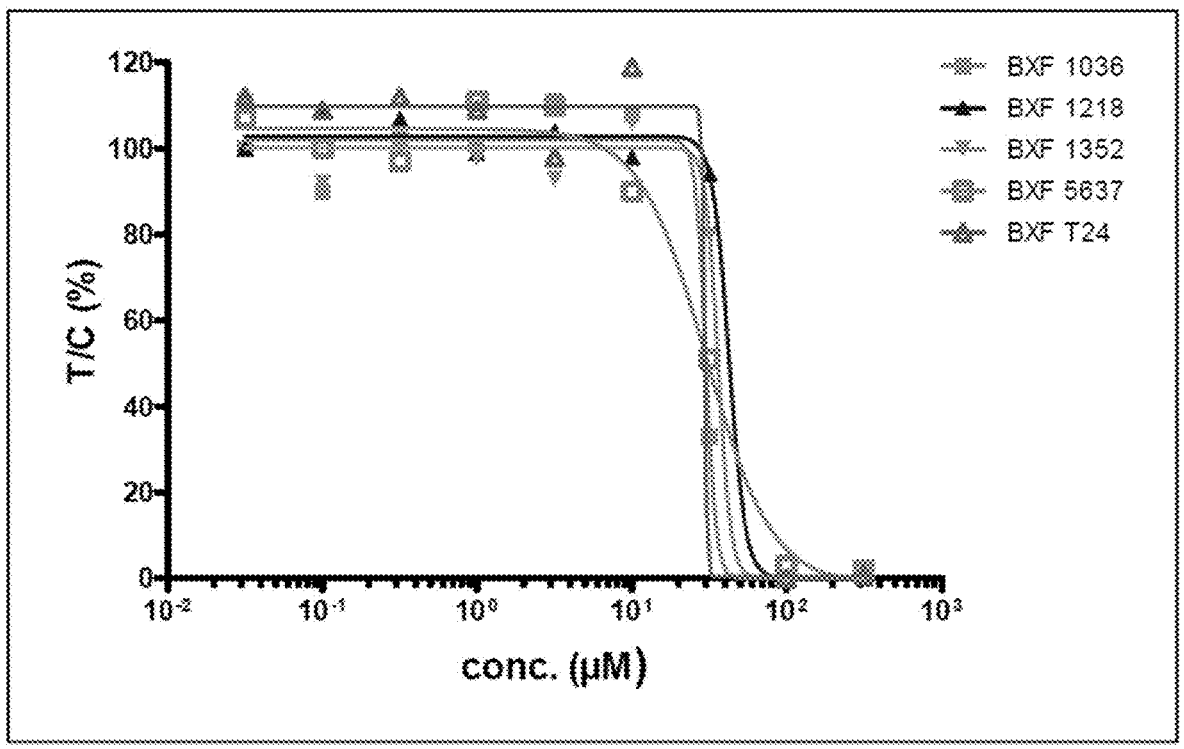
FIG. 3 includes a depiction of a 3D assay of terconazole against human bladder cancer cells.
Figure 4:
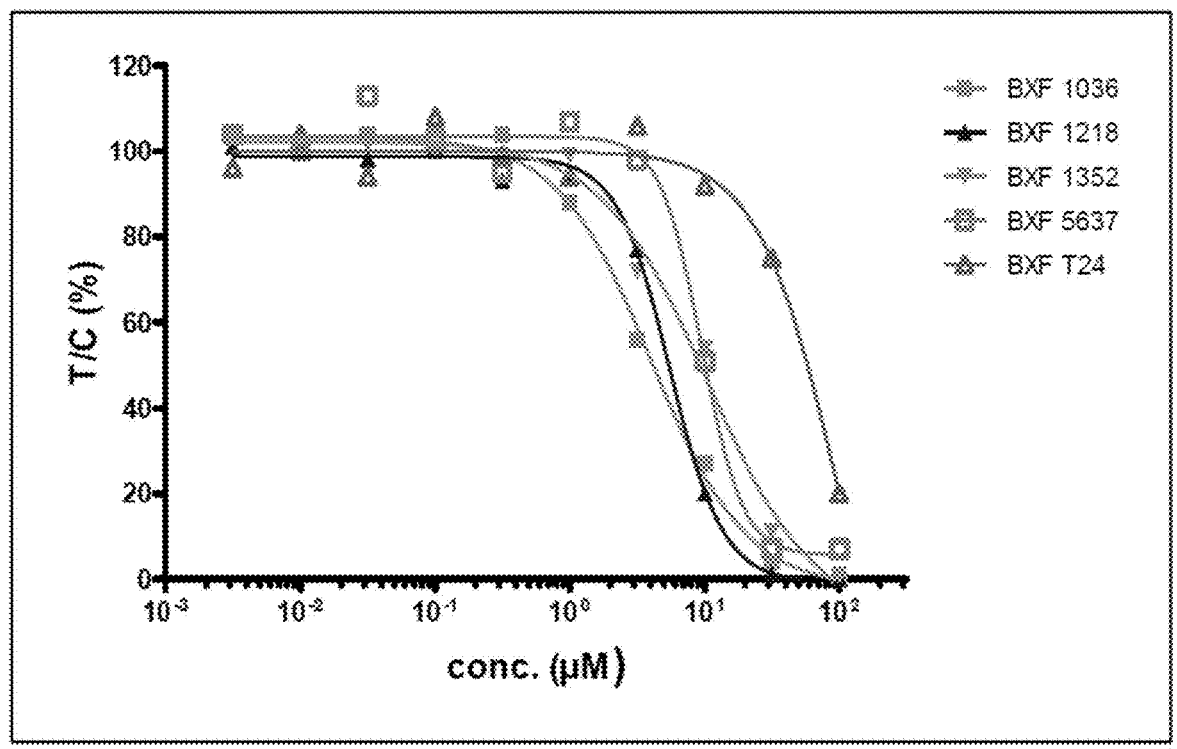
FIG. 4 includes a depiction of a 3D assay cisplatin against human bladder cancer cells.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

In normal adult tissues, neovascularization is required only for repair of tissue injury. In malignant tissues, neovascularization is required for tumors to grow beyond a certain size and to metastasize to new sites. A fine balance between stimulatory and inhibitory factors produced by the tumor and the surrounding stroma regulates new blood vessel development. Bladder tumors produce high levels of multiple angiogenic stimulatory factors, including vascular endothelial growth factor (VEGF), basic fibroblast growth factor (bFGF), and interleukin-8. Levels of these factors correlate with stage and outcome. Micro-vessel density, a surrogate marker for angiogenic activity, is a predictor of disease progression, vascular invasion, lymph node involvement, tumor recurrence, and poor survival in cancer. Levels of VEGF and bFGF are inversely associated with prognosis. Based on these findings, it is hypothesized that targeting angiogenesis pathways alone or in combination with standard chemotherapeutic regimens in bladder cancer will lead to improvement in patient outcomes.

Heme oxygenase-1 (HO-1) is a rate-limiting enzyme that catalyzes oxidative degradation of cellular heme, liberating free iron, carbon monoxide (CO) and biliverdin in mammalian cells. In addition to its primary role in heme catabolism, HO-1 exhibits anti-oxidative and anti-inflammatory functions via the actions of biliverdin and CO, respectively. HO-1 is strongly associated with various disease states, including cancer. Several lines of evidence have supported the role of HO-1 in carcinogenesis and tumor progression. HO-1 deficiency in normal cells enhances DNA damage and carcinogenesis. Nevertheless, HO-1 overexpression in cancer cells promotes proliferation and survival. Moreover, HO-1 induces angiogenesis through modulating expression of angiogenic factors. Although HO-1 is an endoplasmic reticulum resident protein, HO-1 nuclear localization is evident in tumor cells of cancer tissues. It has been shown that HO-1 is susceptible to proteolytic cleavage and translocates to nucleus to facilitate tumor growth and invasion independent of its enzymatic activity. HO-1 also impacts cancer progression through modulating tumor microenvironments. Elevated heme oxygenase-1 (HO-1) is associated with resistance to chemo- and radiotherapy through anti-apoptotic function. It has been reported that HO-1 is significantly expressed in late stage bladder cancer tissue specimen. High T stage (T2-4) correlated with higher percentage of HO-1 positivity compared with low T stage ($P=0.008$) and high in patients with lymph node metastasis ($P=0.022$) than those without metastasis. Significant up-regulation of HO-1 expression is seen in moderate and heavy smokers compared to light or never smokers. Thus HO-1 can be consider as ideal target site for effective treatment of bladder cancer.

Cancer cells exhibit elevated oxidative stress due to their high metabolic rate. Moreover, they are surrounded by a complex microenvironment and significantly influenced by their interplays with the stromal components, especially the infiltrating inflammatory cells. It is envisioned that the oxidative stress and stimulations by various growth factors and cytokines released from stromal cells are capable of inducing HO-1 gene transcription in tumor cells through activation of various signaling pathways and transcriptional factors, including Nrf2, NF-κB, AP2 and others. Hypoxia has also been shown to induce HO-1 expression. Furthermore, HO-1 gene expression is upregulated by oncogenes, such as Kaposi sarcoma-herpes virus and BCR/ABL kinase. In addition to the regulation at transcriptional level, HO-1 expression is subjected to post-transcriptional regulation. Regulation of HO-1 by mir378 is implicated in lung cancer growth and metastasis. Down-regulation of HO-1 by mir200c enhances the sensitivity of renal cancer cells to chemotoxic agents. Moreover, HO-protein is turnover by ubiquitin-proteasome system. HO-1 is a physiological substrate of TRC8, which is an ER-resident E3 ligase associated with hereditary renal cell cancer and thyroid cancer. The tumor suppressive effect of TRC8 is mediated at least in part via targeting HO-1 for ubiquitination and degradation in cancer cells.

Tumorigenesis is a multistep process in which the accumulation of several genomic mutations is required to initiate the transformation of normal cells to become cancer cells. DNA damage caused by the reactive oxygen species (ROS) is a major source of mutation. HO-1 down-regulation leads to the increase of ROS and DNA damage in cells. Furthermore, CO improves cell survival post irradiation or genotoxin treatment by inducing DNA repair. Therefore, increase in HO-1 expression prevents DNA damage and the initiation of carcinogenesis in normal cells. However, at late phase of tumorigenesis, HO-1 overexpression promotes cancer cell proliferation and invasiveness. HO-1 protects cancer cells from apoptosis induced by chemotoxic agents or irradiation, suggesting its involvement in therapeutic resistance. CO contributes to the resistance of cancer cells to oxidative stress and chemotoxic agents by inhibiting the heme-containing cystathionine β-synthase, which causes reduced PFKFB3 methylation and shift of glucose metabolism to pentose phosphate pathway, resulting in subsequent increase of NADPH to replenish reduced glutathione.

The immune/inflammatory cells recruited to tumor microenviroment have profound effects on cancer progression by modulating inflammatory response and anti-tumor immunity. HO-1 modulates the immune regulatory functions of myeloid cells by suppressing the expression of pro-inflammatory cytokines, such as tumor necrosis factor-α, but promoting the expression of immunosuppressive cytokine, interleukin-10 (IL-10). HO-1 promotes inflammation-associated angiogenesis through up-regulating VEGF expression in macrophages. Furthermore, HO-1 expression in myeloid-derived suppressor cells participates in the suppression of alloreactive T cells. Although HO-1 expression in the stromal macrophages has been seen in the cancer tissues, the impact of HO-1 expression in myeloid cells on cancer progression is less explored. HO-1 expression mediates the immune suppressive function of a stromal macrophage subpopulation expressing fibroblast activation protein-α.

Terconazole is a broad-spectrum antifungal drug effective as first line therapy against candida species infections and used for the local treatment of vulvovaginal candidiasis. Terconazole acts by binding to iron component of fungal cytochrome P450 enzyme lanosterol 14 alpha-demethylase. Terconazole may be represented by the following chemical formula:

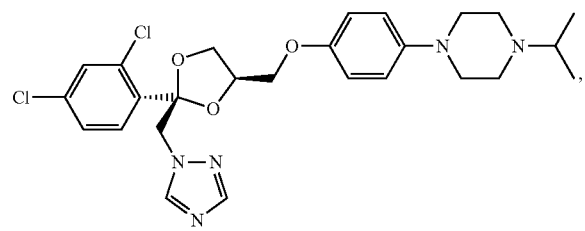

Terconazole is sold as the racemic mixture of the (2S,4R) isomer (depicted above) and the enantiomeric (2R,4S) isomer.

It has been reported by in literature that ketoconazole and terconazole inhibited rat spleen HO-1 activity with $IC_{50}$ of 0.3±0.1 μM and 0.41±0.01 μM respectively.

Disclosed herein are methods of treating bladder cancer in a patient in need thereof by administering an effective amount of terconazole. Unless stated to the contrary, the term terconazole refers both to terconazole free base and pharmaceutically acceptable salts thereof.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, ptoluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made. Pharmaceutically acceptable anions include the conjugate bases of the acids listed above.

Preferably, terconazole may be administered to the subject once daily, twice daily or thrice daily. A typical recommended daily dosage regimen can range from about 5 mg to 2,000 mg, from about 10 mg to 1,000 mg, from about 10 mg to 500 mg, from about 10 mg to 400 mg, from about 10 to 200 mg, from about 10 to 100 mg, from about 10 to 50 mg, from about 50 to 400 mg, from about 100 to 400 mg, or from about 200 to 400 mg.

Preferably, the active agent may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution and sprinkles, transdermal patches, however, other dosage forms such as controlled release formulations, lyophilized formulations, modified release formulations, delayed release formulations, extended release formulations, pulsatile release formulations, dual release formulations and the like. Liquid and semisolid dosage forms (liquids, suspensions, solutions, dispersions, ointments, creams, emulsions, microemulsions, sprays, patches, spot-on), parenteral, topical, inhalation, buccal, nasal etc. may also be envisaged under the ambit of the invention. The inventors of the present invention have also found that the solubility properties of the active agent may be improved by nanosizing thus leading to better bioavailability and dose reduction of the drug.

In one embodiment, terconazole may be present in the form of nanoparticles which have an average particle size of less than 2,000 nm, less than 1,500 nm, less than 1,000 nm, less than 750 nm, less than 500 nm, or less than 250 nm.

Suitable excipients may be used for formulating the dosage form according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, anti-microbial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

Depending on the pathological stage, patient's age and other physiological parameters, and the extent of cancer progression, terconazole may require specific dosage amounts and specific frequency of administrations. Preferably, the active agent may be administered at least once, twice or thrice a day in an amount from 10 mg to 2,000 mg.

In some embodiments, the active agent may be administered such that the total daily dose is in an amount from 10-1,000 mg, 50-1,000 mg, 50-750 mg, 50-500 mg, 100-500 mg, 250-2,000 mg, 500-2,000 mg, 500-1,000 mg, 250-1,000 mg, 250-500 mg, 1,000-2,000 mg, or 1,500-2,000.

Terconazole can be used to treat bladder cancers. In some embodiments, terconazole can reduce tumor size, inhibit tumor growth, alleviate symptoms, delay progression, prolong survival, including, but not limited to disease free survival, prevent or delay bladder cancer metastasis, reduce or eliminate preexisting bladder cancer metastasis, and/or prevent recurrence of bladder cancer.

As used herein, the term "delay" refers to methods that reduce the probability of disease development/extent in a given time frame, when compared to otherwise similar methods that do not include the use of terconazole. Probabilities can be established using clinical trials, but can also be determined using in vitro assays when correlations have been established. In some embodiments, terconazole can inhibit bladder cancer cell proliferation. For instance, at least about 10%, 20%, 30%, 40%, 60%, 70%, 80%, 90%, or 100% of cell proliferation is inhibited. In some embodiments, terconazole can inhibit bladder cancer metastasis. For instance, at least about 10%, 20%, 30%, 40%, 60%, 70%, 80%, 90%, or 100% of metastasis is inhibited.

It can be preferable to diagnose the patient with bladder cancer prior to commencing the therapeutic methods disclosed herein. When the functional consequences are determined using intact cells or animals, one can also measure a variety of effects such as, in the case of bladder cancer associated with tumors, tumor growth, tumor metastasis, neovascularization, hormone release, transcriptional changes to both known and uncharacterized genetic markers (e.g., northern blots), changes in cell metabolism such as cell growth or pH changes, and changes in intracellular second messengers such as cGMP. In the assays of the invention, mammalian bladder cancer polypeptide is typically used, e.g., mouse, preferably human. Tumor cells release an increased amount of certain factors (hereinafter "tumor specific markers") than their normal counterparts. For example, plasminogen activator (PA) is released from human glioma at a higher level than from normal brain cells. See, e.g., "Angiogenesis, tumor vascularization, and potential interference with tumor growth" pp. 178-184 in Mihich (ed. 1985) Biological Responses in Cancer Plenum. Similarly, tumor angiogenesis factor (TAF) is released at a higher level in tumor cells than their normal counterparts. See, e.g., Folkman (1992) Sem Cancer Biol. 3:89-96. Different urine tests are available to look for specific substances released by bladder cancer cells. One or more of these tests may be used along with urine cytology to help determine the bladder cancer. These include the tests for NMP22 (BladderChek) and BTA (BTA stat), the Immunocyt test, and the UroVysion test. In other instances, the patient can be diagnosed with bladder cancer using cystoscopy. In certain embodiments, a patient having detectable amount of one or more of the above markers, after receiving terconazole, with exhibit a 10%, 20%, 30%, 40%, 60%, 70%, 80%, 90%, or 100% reduction in that marker.

Bladder cancer can be characterized by overall stage, 0-IV. Stage 0 is refined by the letters a (designating non-invasive papillary carcinoma) and is (designating non-invasive flat carcinoma, which can be referred to as CIS). The stages can be further refined by one of three categories: T categories refer to the extent the tumor has grown into or beyond the wall of the bladder. T1 refers to cancer that has not grown into the muscle layers of the bladder. T2a indicates the cancer has grown into the inner half of the muscle layer, while T2b indicates the outer half of the muscle layer has been compromised. T3 indicates the tumor has grown into the fatty tissue surrounding the bladder (T3a refers to tumors that are only detectable by microscope, while T3b indicates the tumor can be seen or felt by a physician). T4a indicates the tumor has grown into the stroma of the prostate in men, and into either the uterus or vagina in women. T4b indicates the tumor has reached the pelvic or abdominal wall. N categories refer to the spread in the lymph nodes near the pelvis and along the common iliac artery—N0: There is no regional lymph node spread; N1: The cancer has spread to a single lymph node in the true pelvis; N2: The cancer has spread to 2 or more lymph nodes in the true pelvis; N3: The cancer has spread to lymph nodes along the common iliac artery. M categories refer to spread throughout the body—M0 indicates there are no signs of distant spread and M1 that cancer has spread to distant parts of the body, e.g., distant lymph nodes, bones, lungs, liver, etc.

Terconazole may be administered to patients at various stages of bladder cancer. For instance, terconazole may be administered to a patient at Stage 0a (Ta, N0, or M0), Stage 0 is (Tis, N0, or M0), Stage I (T1, N0, or M0), Stage II (T2a or T2b, N0, or M0), Stage III (T3a, T3b, or T4a, N0, M0), or Stage IV. In some embodiments, terconazole can be administered to patients exhibiting symptoms of bladder cancer that have a genetic predisposition to bladder cancer. For instance, the patient may be SPARC expression positive or negative, or possess one or more mutations in NFL, p53, MIB-1, FEZ1/LZTS1, PTEN, DBCCR1, CDKN2A/MTS1/P6, ERBB2, CDKN2B/INK4B/P15, TSC1, or HRAS1.

Terconazole may be used for the treatment of bladder cancer in mammals, especially humans, in monotherapy mode or in a combination therapy (e.g., dual combination, triple combination etc.) mode such as, for example, in combination with one or more anti-cancer therapeutics. In some instances, terconazole, either alone or in combination therapy, can be administered to a patient that has already undergone a course of BCG therapy. In some embodiments, the patient may receive BCG treatment 1, 2, 3, 4, 5, 6, 7, 8, 9, 10, 11, or 12 months prior to commencing terconazole treatment. In other embodiments, terconazole, either alone or in combination therapy, can be administered to a patient that has not undergone a course of BCG therapy. In yet further embodiments, terconazole, either alone or in combination therapy, can be administered to a patient that is concurrently undergoing a course of BCG therapy.

Terconazole can be administered to bladder cancer patients also receiving one or more immunotherapeutic agents. Immunotherapies include monoclonal antibodie, i.e., checkpoint inhibitors, and oncolytic virus. Oncolytic viruses are genetically engineered or naturally occurring viruses that selectively replicate in and kill cancer cells without harming the normal tissues. The viruses are modified such that they can replicate in cancerous cells, but not healthy cells.

The term "anti-cancer drug" is used in broad sense to include, but is not limited to, oncolytic viruses, monoclonal antibodies, microtubule inhibitors, topoisomerase inhibitors, platins, alkylating agents, and anti-metabolites. Particular agents include modified adenovirus, modified herpes simplex virus, modified reovirus, modified vaccinia virus, atezolizumab, durvalumab, nivolumab, pembrolizumab, ramucirumab, B-701, MK-6018, ALT-801, paclitaxel, gemcitabine, doxorubicin, vinblastine, etoposide, 5-fluorouracil, carboplatin, oxaliplatin, nedaplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalen, 6-mercaptopurine, methotrexate, mitomycin, mitotane, mitoxantrone, pentostatin, procarbazine, rituximab, streptozocin, tamoxifen, temozolomide, teniposide, 6-thioguanine, thiotepa, topotecan, trastuzumab, vincristine, vindesine, and vinorelbine. In certain embodiments, the N-phenyl piperazine can be administered in combination with cisplatin.

In cases of combination therapy, it is possible that a unitary dosage form containing both terconazole and additional anti-cancer agent may be employed. In some instances, the combinations may be provided in form suitable for parenteral application such as but not limited to injection.

In some embodiments, terconazole can be administered as part of a surgical or radiological treatment regime. For instance, a patient may be administered terconazole prior to and/or after undergoing TURBT, partial or radical cystectomy. Likewise, a patient may be administered terconazole prior to and/or after undergoing radiation therapy.

Terconazole can be administered as part of a treatment regime that includes surgical and chemotherapeutic components. The patient, in addition to receiving one or more of the anti-cancer agents identified above, can receive terconazole prior to and/or after undergoing a surgical procedure. In some embodiments, terconazole can be administered as part of a treatment regime that includes radiation therapy and chemotherapeutic components. The patient, in addition to receiving one or more of the anti-cancer agents identified above, can receive terconazole prior to and/or after undergoing radiation therapy. In some embodiments, the chemotherapy includes one or more of cisplatin, fluorouracil, and mitomycin. In other embodiments, terconazole can be administered as part of a treatment regime that includes surgical and immunotherapeutic components. The patient, in addition to receiving one or more of the immunotherapeutic agents identified above, can receive terconazole prior to and/or after undergoing a surgical procedure.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Bladder Carcinoma Efficacy Models

Human bladder cancer cell lines HTB-5, HT-1376 and T-24 were purchased from American Type Culture Collection, USA. Cell lines HTB-5 and HT1376 were routinely cultured in Eagle's Minimum Essential Medium with 10% fetal bovine serum and T-24 in McCoy's 5A medium with 10% fetal bovine serum. All cell lines were maintained at 37° C. in a humidified atmosphere containing 5% $CO_2$.

In vitro cytotoxicity assay: Cells were plated in 96-well cell culture plates ($4 \times 10^3$ cells/well) and were treated with drugs at various concentrations. Treated cells were maintained at 37° C. in 5% $CO_2$ for 48 and 72 hrs. After the incubation antiproliferative activity of test compounds was measured using ProMega Cell Titer aqueous one solution cell proliferation assay kit, viz. CellTiter 96® AQueous One Solution Reagent. Cells were incubated for 1-4 hours at 37° C., 5% $CO_2$ incubator and absorbance was measured at 490 nM using a plate reader. $IC_{50}$ values were determined by plotting compound concentration versus cell viability.

Clonogenic assay: bladder cancer cell lines viz HTB-5, HT-1376 and T-24 cells were plated at different densities i.e. 300 cells/well and 400 cells/well respectively in 3 ml volume per well into six-well plates and incubated overnight at 37° C. in a 5% $CO_2$ incubator. Next day, cells were treated with $IC_{50}$ and $3 \times IC_{50}$ concentrations of ReD for 24 h. Medium with drug was then replaced with medium without drug and plates were further incubated till visible colonies appeared (approximately for 12-14 days). Cells were then fixed with methanol:glacial acetic acid (2:1) and stained with 0.5% crystal violet. After staining for 2-3 min, plates were rinsed twice with D/W, dried and images were captured.

Terconazole showed significant anticancer activity when tested in vitro at varied concentrations against human bladder carcinoma cell lines. T-24, HTB-5 and HT1376.

Example 2: In Vitro 2D Assay

The in-vitro anti-tumor activity of terconazole was assessed in five selected human bladder cancer cell lines. The test compounds were applied at 9 concentrations in half-log increments. As a reference compound cisplatin was tested in parallel. Cells were treated for 96 h with the test compounds. Anti-tumor activity was assessed by using the CellTiter-Blue® Cell Viability Assay. Potency is expressed as absolute $IC_{50}$ and relative $IC_{50}$ values, calculated by non-linear regression analysis.

Individual $IC_{50}$ values for terconazole were in the range from 29.406 µM (BXF 1036) and 46.917 µM (BXF 1218 µM).

The reference compound cisplatin showed concentration-dependent activity in all cell lines tested with a geometric mean absolute $IC_{50}$ value of 8.573 µM.

The in-vitro anticancer activity of terconazole was assessed. Antitumor activity was assessed in five selected bladder cancer cell lines by using the CellTiter-Blue® Cell Viability Assay.

Tumor Cell Lines: In the present study the human bladder cancer cell lines BXF 1036, BXF 1218, BXF 1352, 5637 and T24 were used. BXF 1036, BXF 1218 and BXF 1352 were established at Oncotest from the corresponding human patient derived xenograft. T24 was purchased from ATCC (Rockville, Md., USA) and 5637 was from DSMZ (Braunschweig, Germany). Authenticity of cell lines was confirmed at the DSMZ by STR (short tandem repeat) analysis, a PCR based DNA-fingerprinting methodology. Cell lines were routinely passaged once or twice weekly and maintained in culture for up to 20 passages. All cells were grown at 37° C. in a humidified atmosphere with 5% $CO_2$ in RPMI 1640 medium (25 mM HEPES, with L-glutamine, #FG1385, Biochrom, Berlin, Germany) supplemented with 10% (v/v) fetal calf serum (Sigma, Taufkirchen, Germany) and 0.1 mg/mL gentamicin (Life Technologies, Karlsruhe, Germany).

Cell Proliferation Assay: The CellTiter-Blue® Cell Viability Assay (#G8081, Promega) was used according to manufacturer's instructions. Briefly, cells were harvested from exponential phase cultures, cells/well depending on the cell line's growth rate. After a 24 h recovery period to allow the cells to resume exponential growth, test compounds were added. Compounds were applied at 9 concentrations in half-log increments in duplicate and treatment continued for 96 h. After 96 h treatment of cells, 20 µL/well CellTiter-Blue® reagent was added.

Following an incubation period of up to four hours, fluorescence (FU) was measured by using the Enspire Multimode Plate Reader (excitation k=531 nm, emission k=615 nm). For calculations, the mean values of duplicate/sixfold (untreated control) data were used. Sigmoidal concentration-response curves were fitted to the data points (T/C values) obtained for each cell line using 4 parameter non-linear curve fit (Oncotest Warehouse Software).

The in-vitro anti-tumor activity of terconazole was assessed in five selected human bladder cancer cell lines by using CellTiter-Blue®

Cell Viability Assay: Concentration-dependent activity was also detected for terconazole in all cell lines tested with a geometric mean absolute $IC_{50}$ value of 39.872 µM. Individual $IC_{50}$ values for terconazole were in the range from 29.406 µM (BXF 1036) and 46.917 µM (BXF 1218), indicating a low level of selective activity.

The reference compound cisplatin showed concentration-dependent activity in all cell lines tested with a geometric mean absolute $IC_{50}$ value of 8.573 µM. The selectivity profile of cisplatin was quite similar to CIPDE034 (terconazole), with T24 shown to be the most sensitive and BXF 1352 the most resistant cell line. The $IC_{50}$ values are tabulated in the below table.

| Cell Line | Absolute $IC_{50}$ values (µM) | |
|---|---|---|
| | Terconazole | Cisplatin |
| BXF 1036 | 29.406 | 9.529 |
| BXF 1218 | 46.917 | 7.078 |
| BXF 1352 | 45.864 | 17.059 |
| BXF 5637 | 38.368 | 9.706 |
| BXF T24 | 41.508 | 4.148 |
| Geometric Mean Absolute $IC_{50}$ values (µM) | 39.872 | 8.573 |

Example 3: In Vitro 3D Assay

In the present study, terconazole and cisplatin were evaluated for their ability to inhibit anchorage independent growth and ex vivo colony formation of tumor cells in semi-solid medium. The compounds were tested against 5 human tumor cell lines of bladder cancer. Test concentrations ranged, from 0.0316 µM to 316.2 µM (terconazole), or from 0.00316 µM to 100 µM (cisplatin).

Terconazole and cisplatin inhibited colony formation in a concentration-dependent manner. Terconazole inhibited colony formation of all bladder cancer cell lines tested with $IC_{50}$ values ranging from 29.56 µM to 40.05 µM. $IC_{50}$ values were very similar, thus differential anti-tumor efficacy was not that pronounced. Bottom plateaus of the concentration-effect curves of responding tumor models were 0%, indicating clear inhibition of tumor colony growth.

Cisplatin inhibited colony formation with a mean relative $IC_{50}$ value of 9.71 µM (mean absolute $IC_{50}$ value=9.93 Bottom plateaus of the concentration-effect curves of the responding tumor models were <10%, indicating clear inhibition of tumor colony growth. Based on relative $IC_{50}$ values, above average activity was observed against ⅛ tumor models (cell line BXF 1036).

Terconazole and the reference compound cisplatin were investigated for anticancer activity ex vivo in five human tumor cell lines of bladder cancer. Tests were carried out using a 3D clonogenic assay in 96-well format with image based read-out. The aim of the study was to investigate antitumor potency and tumor type selectivity of the compound.

Clonogenic Assay Procedure: The clonogenic assay was carried out in a 96 well plate format using ultra low attachment plates. For each test, cells were prepared as described above and assay plates were prepared as follows: each test well contained a layer of semi-solid medium with tumor cells (50 and a second layer of medium supernatant with or without test compound (100 The cell layer consisted of $2·10^3$ to $3·10^3$ tumor cells per well, which were seeded in 50 µL/well cell culture medium (IMDM, supplemented with 20% (v/v) fetal calf serum, 0.01% (w/v) gentamicin, and 0.4% (w/v) agar. After 24 hours the test compounds were added after serial dilution in cell culture medium, and left on the cells for the duration of the experiment (continuous exposure, 100 µl drug overlay). Every plate included six untreated control wells and drug-treated groups in duplicate at 9 concentrations. Cultures were incubated at 37° C. and 7.5% $CO_2$ in a humidified atmosphere for 8 to 13 days and monitored closely for colony growth using an inverted microscope. Within this period, ex vivo tumor growth led to the formation of colonies with a diameter of >50 µm. At the time of maximum colony formation, counts were performed with an automatic image analysis system (Bioreader 5000-Wa Biosys GmbH). 48 hours prior to evaluation, vital colonies were stained with a sterile aqueous solution of 2-(4-iodophenyl)-3-(4-nitrophenyl)-5-phenyltetrazolium chloride (1 mg/ml, 100 µl/well)

Terconazole inhibited colony formation in a concentration-dependent manner. The mean relative $IC_{50}$ value was determined as 33.48 µM (mean absolute $IC_{50}$ value=33.88 µM). Bottom plateaus of the concentration-effect curves of responding tumor models were 0%, indicating clear inhibition of tumor colony growth. $IC_{50}$ values were very similar, thus differential anti-tumor efficacy was not that pronounced.

The $IC_{50}$ values are tabulated in the table below.

| Cell Line | Absolute $IC_{50}$ values (µM) | |
|---|---|---|
| | Terconazole | Cisplatin |
| BXF 1036 | 29.67 | 3.97 |
| BXF 1218 | 40.27 | 5.36 |
| BXF 1352 | 36.59 | 8.65 |
| BXF 5637 | 30.80 | 10.08 |
| BXF T24 | 33.15 | 52.99 |
| Geometric Mean Absolute IC50 values (µM) | 33.88 | 9.93 |

Example 4: In Vitro Combination Study

Summary: Terconazole was tested alone and in combination with cisplatin in order to investigate the ability to inhibit tumor cell growth of bladder cancer cell lines in a 5×5 matrix combination format. Efficacy of the combinations was assessed by measuring anchorage-independent growth and in vitro tumor colony formation using a 3D clonogenic assay in cell lines BXF 1036L, BXF 1218L, and BXF T24.

Terconazole tested as single agent inhibited colony formation of tumor cells seeded in soft-agar in a concentration-dependent manner with $IC_{50}$ values ranging from 27.1 µM (BXF 1036L) to 59.8 µM (BXF T24). Cisplatin was active against the cell lines BXF 1036L and BXF 1218L ($IC_{50}$ of 6.09 µM and 6.8 respectively) while being less active against BXF T24 ($IC_{50}$=77.4 µM).

Additive effects were observed for the combination of terconazole with cisplatin in bladder cancer cell lines BXF 1036L, BXF 1218L, and BXF T24.

The objective of this study was to assess anti-tumor efficacy of CIPDE033 and CIPDE034 in combination with cisplatin in a 5×5 matrix combination format against various bladder cancer cell lines. Efficacy of the combinations was assessed by measuring anchorage-independent growth and in vitro tumor colony formation using a 3D clonogenic assay in cell lines BXF 1036L, BXF 1218L, and BXF T24. The Bliss independence methodology was used for data analysis, in order to identify possible synergistic effects.

The compounds were tested in ovarian cell lines, namely BXF 1036L, BXF 1218L, and BXF T24. Cells lines of BxF 1036L and BXF 1218L were established at Oncotest in Freiburg from the corresponding patient-derived xenografts. BXF T24 cells were obtained from American Type Culture Collection (Rockville, Md., USA). Authenticity of cell lines was confirmed at the DSMZ by STR analysis.

Cultivation of Cell Lines: Cell lines were routinely passaged once or twice weekly and maintained in culture for up to 20 passages. Cells were grown at 37° C. in a humidified atmosphere with 5% $CO_2$ in RPMI 1640 medium (25 mM HEPES, with L-glutamine, Biochrom) supplemented with 10% (v/v) fetal calf serum and 0.1 mg/mL gentamicin. The percentage of viable cells was determined in a Neubauer-hemocytometer using trypan blue exclusion.

3D Clonogenic Assay Procedure: The clonogenic assay was carried out in a 96 well plate format using ultra low attachment plates. For each test cells were prepared as described above, and assay plates were prepared as follows: each test well contained a layer of semi-solid medium with tumor cells (50 µl), and a second layer of medium supernatant with or without test compounds (100 µl). The cell layer consisted of $5 \cdot 10^3$ to $7.5 \cdot 10^3$ tumor cells per well, which were seeded in 50 µl/well cell culture medium (IMDM, supplemented with 20% (v/v) fetal calf serum, 0.01% (w/v) gentamicin, and 0.4% (w/v) agar). After 24 h, the soft-agar layer was covered with 90 µl of the same culture medium without agar, and compounds were added after serial dilution in DMSO and transfer in cell culture medium and left on the cells for the duration of the experiment (continuous exposure, 100 µL total drug overlay). Every plate included six untreated control wells and drug-treated groups. Cultures were incubated at 37° C. and 7.5% $CO_2$ in a humidified atmosphere for 8 to 13 days and monitored closely for colony growth using an inverted microscope. Within this period, ex vivo tumor growth led to the formation of colonies with a diameter of >50 µm. At the time of maximum colony formation, counts were performed with an automatic image analysis system (CellInsight NXT, Thermo Scientific). 48 hours prior to evaluation, vital colonies were stained with a sterile aqueous solution of 2-(4-iodophenyl)-3-(4-nitrophenyl)-5-phenyltetrazolium chloride (1 mg/ml, 100 µl/well).

Results and Discussion: The ability of terconazole to inhibit ex vivo colony formation of cells as single agent and in combination with cisplatin was examined in 3 bladder cancer cell lines (BXF 1036L, BXF 1218L and BXF T24). Information about single agent efficacy was derived from monotherapy controls of the 5×5 combination matrix. Terconazole tested as single agent inhibited colony formation of tumor cells seeded in soft-agar in a concentration-dependent manner with $IC_{50}$ values ranging from 27.1 µM (BXF 1036L) to 59.8 µM (BXF T24). Cisplatin was active against the cell lines BXF 1036L and BXF 1218L ($IC_{50}$ of 6.09 µM and 6.8 µM, respectively) while being less active against BXF T24 ($IC_{50}$=77.4 µM). Additive effects were observed for the combination of terconazole with cisplatin in bladder cancer cell lines BXF 1036L, BXF 1218L, and BXF T24.

Terconazole and cisplatin inhibited colony formation of BXF 1036L cells seeded in soft agar in a concentration-dependent manner. This is also reflected in the matrix combination, where activity of the different combinations was observed at higher concentrations of both compounds.

Figure 5:
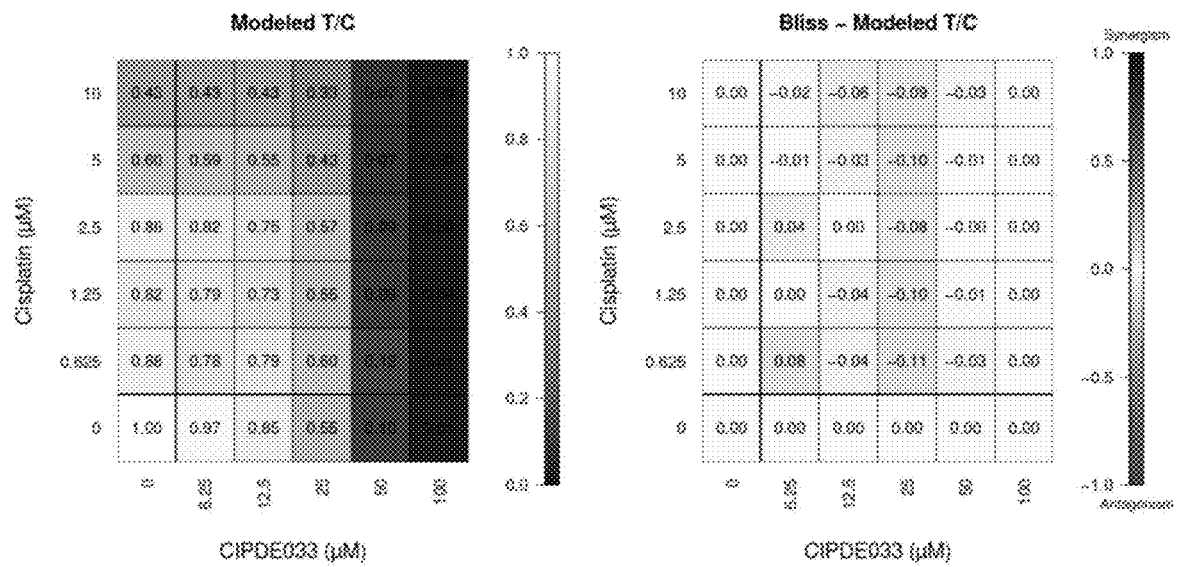
FIG. 5 includes a depiction of the anti-tumor efficacy of terconazole (CIPDE033) in combination with cisplatin in BXF 1036L; A) Modeled T/C, which is the mean of experimental T/C for each pair of conditions in the combination matrix. B) Bliss index, which is the difference of Bliss neutral and modeled T/C for each pair of conditions FIG. 6 includes a depiction of the anti-tumor efficacy of terconazole (CIPDE033) in combination with cisplatin in BXF 1218L. A) Modeled T/C, which is the mean of experimental T/C for each pair of conditions in the combination matrix. B) Bliss index, which is the difference of Bliss neutral and modeled T/C for each pair of conditions.

Bliss independence analysis showed that overall an additive effect of the combinations was obtained, i.e. neither synergy nor antagonism. The color coding of the tiles in the heatmap show that there is no consistent concentration-dependent effect pointing towards synergy (BI>0.15) or antagonism (BI<−0.15). The results are depicted in FIG. 5.

Terconazole and cisplatin inhibited colony formation of BXF 1218L cells seeded in soft agar in a concentration-dependent manner. This is also reflected in the matrix combination, where activity of the different combinations was observed at higher concentrations of both compounds.

Figure 6:
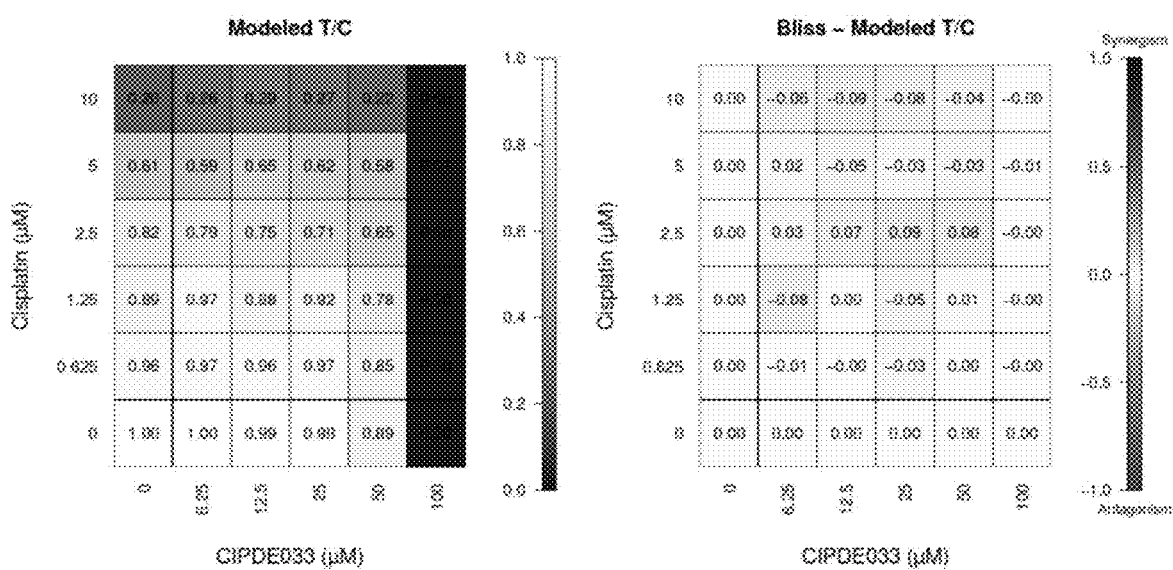

Bliss independence analysis showed that overall an additive effect of the combinations was obtained, i.e. neither synergy nor antagonism. The color coding of the tiles in the heatmap show, that there is no consistent concentration-dependent effect pointing towards synergy (BI>0.15) or antagonism (BI<−0.15). The results are depicted in FIG. 6.

Terconazole and cisplatin inhibited colony formation of BXF T-24 cells seeded in soft agar in a concentration-dependent manner. This is also reflected in the matrix combination, where activity of the different combinations was observed at higher concentrations of both compounds.

Figure 7:
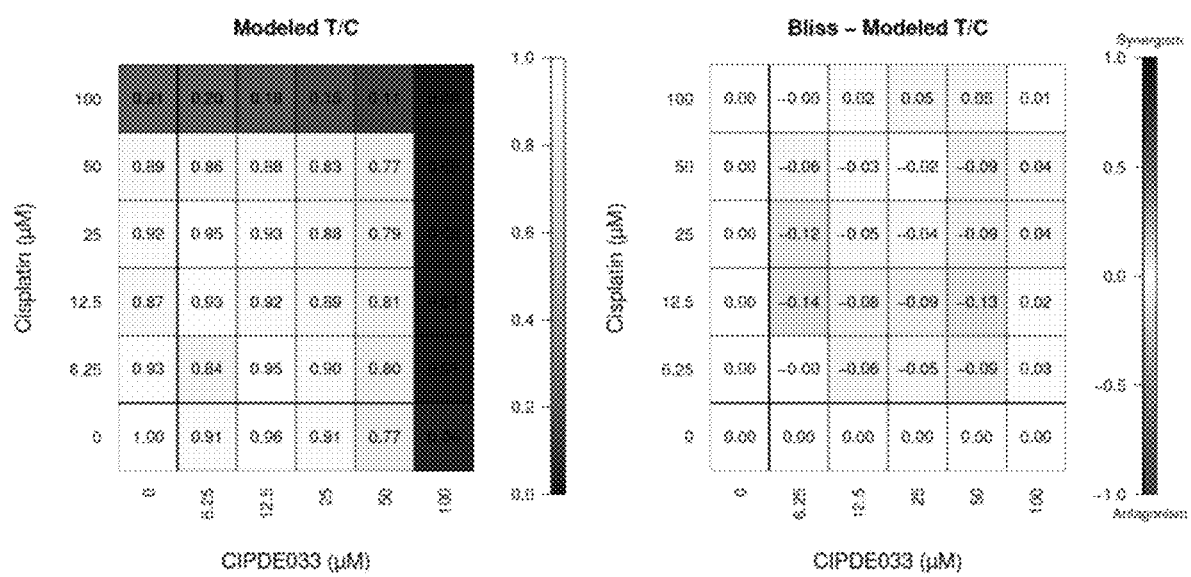
FIG. 7 includes a depiction of the anti-tumor efficacy of terconazole (CIPDE033) in combination with cisplatin in BXF T-24. A) Modeled T/C, which is the mean of experimental T/C for each pair of conditions in the combination matrix. B) Bliss index, which is the difference of Bliss neutral and modeled T/C for each pair of conditions

Bliss independence analysis showed that overall an additive effect of the combinations was obtained, i.e. neither synergy nor antagonism. The color coding of the tiles in the heatmap show, that there is no consistent concentration-dependent effect pointing towards synergy (BI>0.15) or antagonism (BI<−0.15). The results are depicted in FIG. 7.

Example 5: Compositions

Terconazole Soft Gelatin Capsule

| Ingredient | Qty. mg/unit |
| --- | --- |
| Terconazole | 20-400 |
| D-alpha-tocopheryl polyethylene glycol 1000 succinate (TPGS) | 250-550 |
| Polyethylene glycol 400 | 250-400 |
| Polyethylene glycol 400 | 25-40 |

1. Load D-alpha-tocopheryl polyethylene glycol 1000 succinate (TPGS) in a suitable stainless steel jacketed vessel and heat to 50° C. until liquefied.
2. Heat Polyethylene glycol 400 (90%) in a separate stainless steel vessel to 50° C. and add to the liquefied material of step 1 slowly.
3. Mix the ingredients of step 2 using a suitable stirrer until homogenous solution obtained.
4. Increase the temperature of the homogenous solution to 65° C., and add Terconazole to the solution of step 3 under constant stirring and dissolved.
5. Add remaining quantity of Polyethylene glycol 400 (10%) to the solution of step 4 and cool the solution to room temperature.
6. Apply vacuum to remove the entrapped air.
7. Fill mixture using in white opaque soft gelatin capsules (size 12, oblong) using a capsule-filling machine. The capsules were further dried to a moisture level of 3-6% and shell hardness of 7-10 N and packed in a suitable container.

Terconazole tablets (Hot Melt Extrusion technique)

TABLE 2A (Terconazole Granule)

| Ingredients | Formula I (%) | Formula II (%) | Formula III (%) |
| --- | --- | --- | --- |
| Terconazole | 100 | 100 | 100 |
| Poloxamer 407 | 70 | 80 | 90 |
| Sentry Polyox WSR N80 (PEO) | 30 | 20 | 10 |

TABLE 2B (Terconazole Tablet)

| Ingredients | Qty/Tab (mg) |
| --- | --- |
| Terconazole granules (HME) | 20-300 |
| Lactose monohydrate. | 40-120 |
| Microcrystalline Cellulose | 75-225 |
| Hypromellose | 60-90 |
| Croscarmellose sodium | 15-45 |
| Colloidal anhydrous silica | 2-6 |
| Magnesium stearate | 1-5 |
| Talc | 1-5 |
| Opadry ready mix | 10-20 |
| Purified water | Qs |

Procedure: The composition as covered under Table 2 is prepared using following process:

Terconazole Granule:
1. Use hot melt extruder (Make: Thermo Scientific Instruments) in the preparation of extrudates
2. Shift all powders through specified mesh
3. Blend the powders of step 1 in V-shell blender prior to extrusion
4. Blend the powder of step 2 in the hopper located at the head of vertical screw such that the material is flood fed by gravity for residence time of approximately 3 minutes.
5. Shear the extrudate of step 4 after exiting the die and allowed to cool at ambient conditions.
6. Pass the extrudates of step 5 again through quadro co-mill to get granules of desired size.

Terconazole Tablet:
1. Blend Terconazole granules obtained in part A further in V—shell blender with lactose monohydrate, microcrystalline cellulose, hypromellose, croscarmellose sodium, colloidal anhydrous silica, and talc previously passed through suitable sieves.
2. Lubricate the blend in a V-shell blender with magnesium stearate previously sifted through suitable sieve.
3. Compress the lubricated blend of step 2 into tablets using suitable tooling using a tablet compression machine.
4. Coat the tablets using a film coating dispersion. (The film coating dispersion was prepared by dispersing the opadry ready mix in purified water).

Terconazole Tablets

| Ingredients | Quantity mg/tablet |
| --- | --- |
| Terconazole | 20-300 |
| Lactose monohydate | 30-150 |
| Microcrystalline cellulose (Avicel PH 101) | 40-160 |
| Pregelatinized starch | 30-60 |
| Croscarmellose sodium | 15-45 |
| Poloxamer 188 (Pulmonic F 68) | 5-20 |
| Silicon dioxide colloidal | 2.5-10 |
| Magnesium stearate | 3-10 |
| Purified water | q.s |

1. Shift Terconazole, lactose monohydate, pregelatinized starch, and a portion (one-half) of croscarmellose sodium in a mixer through #30 sieve.
2. Load the sifted powders of step 1 in a suitable mixer/granulator and mix the materials for 20 minutes.
3. Dissolve poloxamer 188 in sufficient quantity of purified water, and use it to wet granulate the blend of step 2.
4. Dry the granules of step 3 in a fluidized-bed dryer until the LOD is 2% or less.
5. Pass the dried granules of step 4 through a screen, or mill them to obtain granules of the desired size (1-3 mm).
6. Blend the sized granules of step 5 with silicon dioxide (previously sifted through #60 Sieve), microcrystalline cellulose (pre sifted through #30 sieve), and the remaining croscarmellose sodium in octagonal blender for 7 minutes.
7. Lubricate the blend of step 6 by adding magnesium stearate (previously sifted through #60 Sieve) to the blend of step 6 and further blending for 3 minute.
8. Compress lubricated blend of step 7 into tablets using suitable tooling using a tablet compression machine.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A kit comprising an active agent for the treatment of bladder cancer, wherein the active agent consists of:
   (a) terconazole; and
   (b) an anti-cancer agent selected from the group consisting of cisplatin, carboplatin, oxaliplatin, and nedaplatin.

2. The kit according to claim 1, wherein the anti-cancer agent is cisplatin.

3. A composition comprising an active agent for the treatment of bladder cancer, wherein the active agent consists of:
   (a) terconazole; and
   (b) an anti-cancer agent selected from the group consisting of cisplatin, carboplatin, oxaliplatin, and nedaplatin.

4. The composition according to claim 3, wherein the anti-cancer agent is cisplatin.

* * * * *